United States Patent [19]

Sneider

[11] Patent Number: 4,674,510

[45] Date of Patent: Jun. 23, 1987

[54] DISPOSABLE SANITARY BREAST PAD FOR A BRASSIERE

[76] Inventor: Vincent R. Sneider, 3422 Hallcrest Dr., NE., Atlanta, Ga. 30319

[21] Appl. No.: 917,387

[22] Filed: Oct. 9, 1986

[51] Int. Cl.4 .............................................. A41C 3/10
[52] U.S. Cl. .................................................. 128/481
[58] Field of Search .............. 128/481, 480, 461, 505, 128/150, 479; 604/366, 370, 375, 380, 383, 385 R, 387

[56] References Cited

U.S. PATENT DOCUMENTS

| 2,082,503 | 6/1937 | Meadows | 128/481 |
| 2,959,173 | 11/1960 | Douthit | 128/481 |
| 3,297,036 | 1/1967 | Williams | 128/505 |

Primary Examiner—Doris L. Troutman
Attorney, Agent, or Firm—Ralph R. Roberts

[57] ABSTRACT

The disposable breast pad of this invention is generally circular and there is formed therein a predetermined angle of score lines providing fold assists. The barrier sheet of thin, pliable plastic material is an impervious barrier to the passage therethrough of excess fluid from the breast. The disposable pad is folded at radial edge portions to provide a manipulated overlay and form a conically-shaped cup. The outer surface of the barrier sheet has an applied adhesive which not only retains the overlap edge portions, but also when exposed provides a non-toxic contact-adhesive providing retention of the pad in the brassiere cup until the pad is to be removed and discarded. The barrier sheet is not cut radially; therefore, unwanted leakage therethrough cannot occur. Folding of a portion of the pad produces three or five thicknesses at the overlap.

21 Claims, 18 Drawing Figures

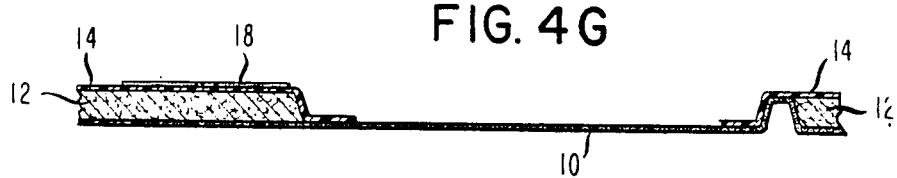
FIG. 4G
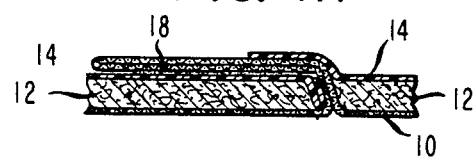
FIG. 4H
FIG. 5A
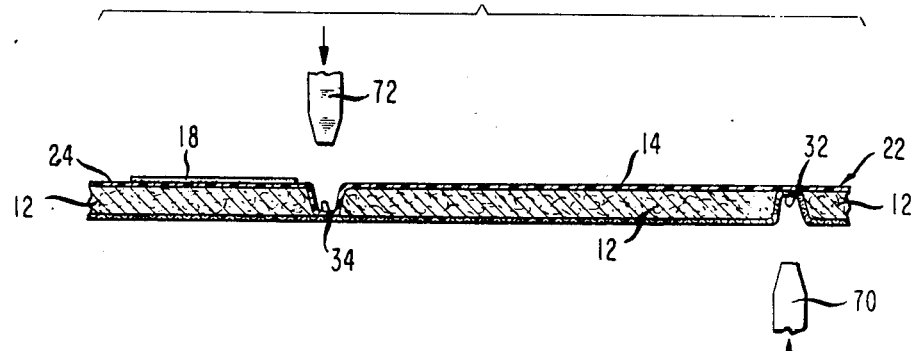
FIG. 5B
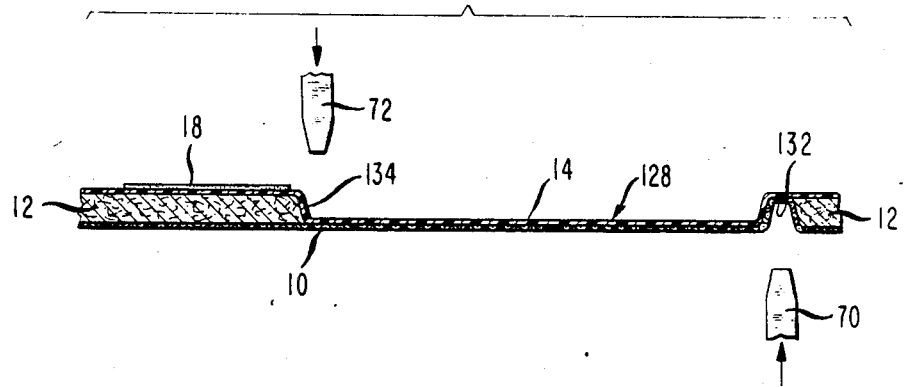
FIG. 5C
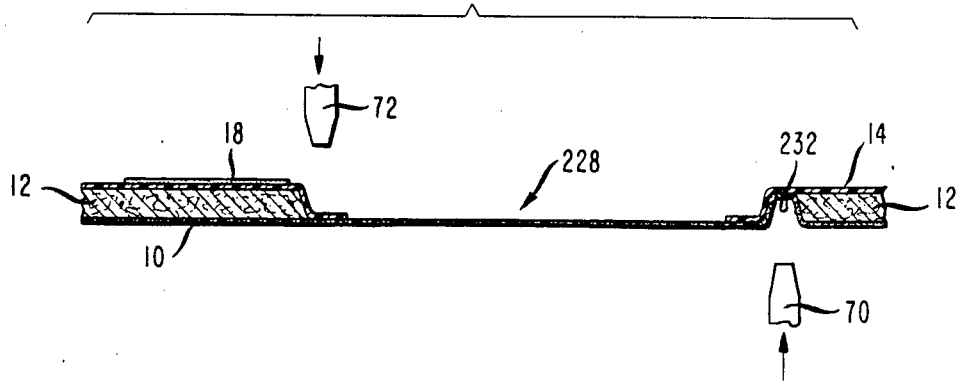

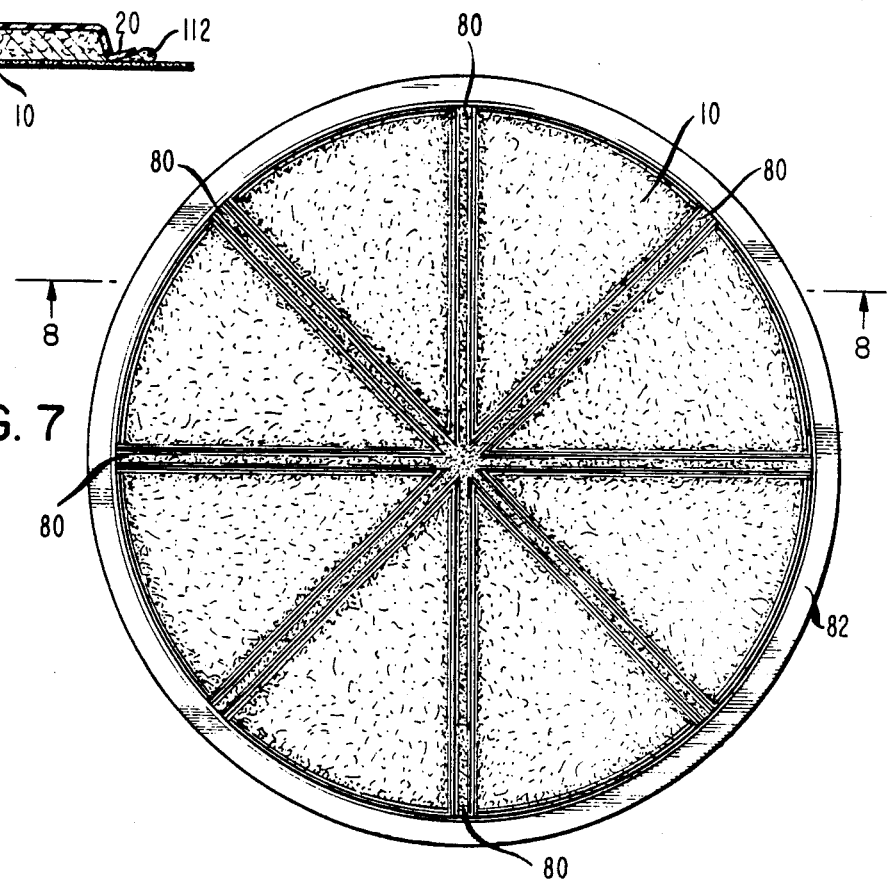

DISPOSABLE SANITARY BREAST PAD FOR A BRASSIERE

CROSS-REFERENCE TO RELATED PATENT

To the extent applicable, this invention pertains to my U.S. Pat. No. 3,738,362 as issued June 12, 1973. My new invention provides a disposable pad similar to this pad, but with an improved construction to make the product of this invention fail-safe in application and use.

BACKGROUND OF THE INVENTION

1. Field of the Invention

As classified in and by the United States Patent Office, this invention is believed to relate to the general class entitled "Surgery" and more particularly to the subclasses of "bandaging," "pads" and "receptors."

2. Description of the Prior Art

Sanitary pads, breast pads and the like are, of course, well known in both commerce and the art, and a constant program of research has brought improvements in the art to a more or less high degree of development. It is to be noted that many women, particularly at times associated with childbirth, are troubled with the problem of a light breast discharge. Many pads have been brought to the marketplace, but these have problems in that they are too bulky and uncomfortable for everyday use and they present various other problems in use and in assembly of use. Thus, there is a need for a pad which will receive such discharges while being easy to assemble and to wear every day and without discomfort. Also of note are the references noted in the issued U.S. Pat. No. 3,738,362, which are: U.S. Pat. No. 2,767,402 to PAUK as issued October 1956; U.S. Pat. No. 3,161,200 as issued to BRICKMAN in December 1964; U.S. Pat. No. 3,356,090 as issued to PIANTINGA et al in December 1967, and U.S. Pat. No. 3,502,083 as issued to HOWARD et al in March 1970.

My above-referenced patent shows a pad which in its inital condition is a flat, disposable body-contact pad of generally circular platform and having a local, generally radially-extending cut portion, with said pad being adapted to be removably carried by self-adhesion to an inner concave surface of a brassiere. This pie-shaped cut requires a fold and securing of the V-cut edge portions. When the fold and securing is less than precisely performed, a small leak hole may occur and, if and when present, may cause the excess fluid or fluids to flow to the outer surfaces of the pad. This may result in the brassiere to be wetted, soiled or, and more importantly, cause the mother's dress or blouse to be wetted if not soiled. The present invention precludes the leakage of any excess fluid through a hole in the center area of the pad.

In addition to the above-noted patents, attention is directed to U.S. Pat. No. 1,984,253 as issued to COX on Dec. 11, 1934. This patent shows a breast protector, but the cups are connected together as in FIG. 3 and the entire protector is discarded. In accordance with the teaching, this protector would be expensive to make. Attention is also directed to U.S. Pat. No. 2,748,771 as issued to RICHARDS on June 5, 1956. The receptor is essentially of plastic having a portion with perforations and requires a separate absorbent pad 21 for each receptor. Also of note in U.S. Pat. No. 4,333,471 as issued to NAKAI on June 8, 1982, in which a nipple cover uses pressure-sensitive adhesive to retain this cover to the user's skin. The pad of applicant does not have such an adhesive attachment arrangement.

SUMMARY OF THE INVENTION

This invention may be summarized, at least in part, with reference to its objects. It is an object of this invention to provide, and it does provide, a disposable, sanitary breast pad for a brassiere, which pad has a thin, moisture-impervious backing sheet absent a pie- or wedge-shaped cutout sheet.

It is a further object to provide, and it does provide, a disposable pad with improved fluid-retention capability which is initially planar in configuration with the fill portion and with a porous cover layer. The fill, cover and backing are formed with radially-formed fold areas so the impervious moisture-impervious backing sheet is not with a radial cut. The thin pad, backing and cover are sufficiently flexible so as to be formed into a cup shape and, with an outer strip of adhesive, secure this disposable pad as a cup within the brassiere cup without the use of snaps, pins or special retaining means.

In brief, this disposable, sanitary breast pad for brassieres in the initial condition is generally planar and has a moisture-impervious plastic backing sheet, usually of polyethylene, and quite thin and pliant. This backing barrier sheet is usually less than one mil in thickness and circular. Secured to this backing member and interior of the edges of the backing sheet is an absorbent layer or sheet. This absorbent layer may be plied or unplied and is usually thin and non-bulky so that in use the protector pad does not occupy excessive space. This fill layer is provided with a fold area which is V- or pie-shaped.

A porous and pliant outer cover or top sheet is conventionally made of a non-woven fabric of a non-toxic thermoplastic material having an outer diameter sized to match the plastic backing sheet. This outer cover overlays and is generally in coincidence with periphery of the backing sheet. There is a continuous edge portion in which no fill is present, with the backing and outer coverheat-sealed together. At this same time, male and female folding radial score lines are provided in said constructed pad. A tear strip of thin plastic and having an adhesive coat is applied to the backing sheet so as to provide a securing of the pad and a radial fold edge of the pad as and when formed into a cup shape.

In addition to the above summary, the following disclosure is detailed to insure adequacy and aid in understanding of the invention. This disclosure, however, is not intended to cover each new inventive concept no matter how it may later be disguised by variations in form or additions of further improvements. For this reason, there has been chosen a specific embodiment of a disposable, sanitary breast pad as adopted for use as a replaceable unit in a brassiere cup and showing a preferred means for constructing and use, particularly in the folding of a pie-shaped portion, and forming this pad into a convex cup shape insertable into a brassiere. This specific embodiment has been chosen for the purposes of illustration and description as shown in the accompanying drawings wherein:

BRIEF DESCRIPTION OF THE DRAWINGS

FIGS. 5 A, 5 B and 5 C represent sectional views, diagrammatically depicting heat-sealing dies providing means for forming the male and female groove portions in the pad;

FIG. 6 represents a sectional view showing fill fluff extending beyond the peripheral edge of the pad, this fluff providing a soft-edge portion for the disposable pad;

FIG. 7 represents a plan view, partly diagrammatic, and showing the disposable pad of this invention with added impressed, radially-disposed fold lines providing assisting means for forming the pad into a cup shape;

FIG. 8 represents a sectional view, partly diagrammatic, showing heat-sealed line portions and a pressure-impressed portion intermediate thereof, and FIG. 9 represents an isometric view, very fragmentary, and showing the pad structure in which an inner cover-retaining member is pierced to increase the flow capability through the inner cover material.

In the following description and in the claims, various details are identified by specific names for convenience. These names are intended to generic in their application. Corresponding reference characters refer to like members throughout the several figures of the drawings.

The drawings accompanying, and forming part of, this specification disclose details of construction for the purpose of explanation, but structural details may be modified without departure from the concept and principles of the invention and the invention may be incorporated in other structural forms than shown.

EMBODIMENT OF FIG. 1

Figure 1:
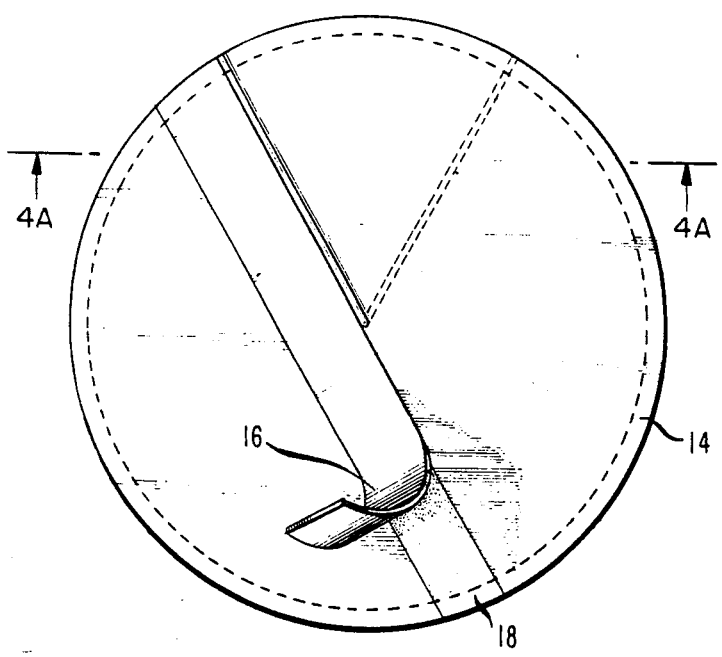
FIG. 1 represents a plan view, partly diagrammatic, and showing the disposable pad of this invention in a flat initial condition, with a tear strip partly removed from an adhesive portion.

In FIG. 1, the disposable, sanitary breast pad for a brassiere is depicted. A moisture-impervious, thin, pliant barrier sheet 10 is preferably made of an inexpensive plastic member which is usually a sheet of one-half to one mil in thickness. A thermoplastic sheet member is contemplated to be provided as a securing of the sandwich of the members is contemplated to be by heat-sealing. To this barrier sheet 10 is secured an absorbent fill layer 12 which may be one- to five-thousandths of an inch in thickness, but this thickness is not critical. It is contemplated that bulk not be present in this fill, although absorbent capability is needed and essential. The fill may be of plied or unplied material or combinations thereof as selected for use. Where the capability for absorbing excess fluids needs to be increased, the fill 12 may be increased in thickness or changed as to material.

A porous, thin and pliant flexible inner cover-sheet member 14 may be a non-woven fabric which contains a non-toxic thermoplastic component or at least a portion thereof. This coversheet member is usually from two- to ten-thousandths of an inch in thickness. The outer portion is caused to overlay the barrier sheet so as to be secured by heat-sealing or the like. This heat-sealing may include radial portions that provide fold score assists for a purpose to be described hereinafter.

Also seen in FIG. 1 is a tear strip 16 having an adhesive portion 18. Initially, this adhesive is usually a coating on this tear strip which is secured to the disposable pad until the pad is prepared for use. This strip 16 is of any selected width, but is conventionally from one-quarter to three-quarters of an inch. The adhesive 18 is commercially available and is known as self-sticking when the protective tear strip 16 is removed. Although this adhesive 18 may be over the entire outer pad area, it is usually as a strip with the protective material tear strip 16 for the adhesive preferably kept to a minimum. The adhesive 18 when exposed is made of sufficient area and capability to retain a formed inserted and disposable pad. This adhesive is selected so as to be non-toxic and is usually of a rubber-base variety. This adhesive when pressed against barrier sheet 10 is disposed to remain on sheet 10 and also to resist permanent adhesion to the brassiere cup within which said pad is placed. The pad is sealed at its outer edge 20 by means such as heat-sealing.

EMBODIMENTS OF FIG. 2 AND FIG. 3

Figure 2:
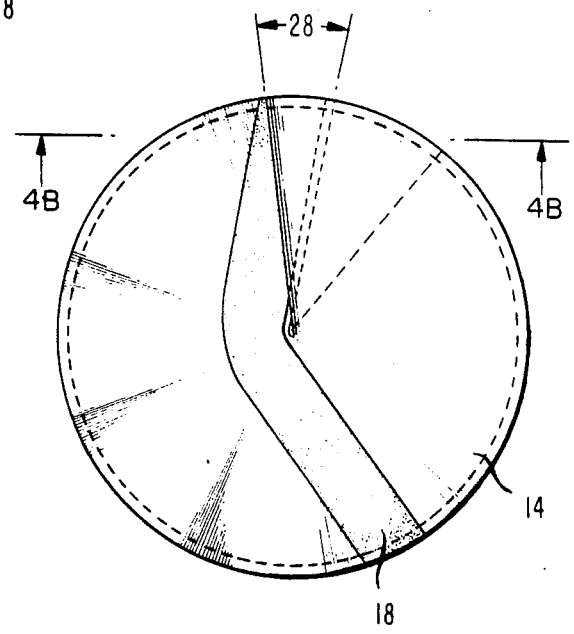
FIG. 2 represents a plan view, partly diagrammatic, of the pad of FIG. 1 and showing the pad manipulated and folded to provide a conical shape and disposable pad.

In FIG. 2, the disposable breast pad is shown with tear strip 16 removed and with the adhesive portion 18 exposed for use. In FIG. 2, the right diagonal-edge portion, identified as 22, is brought over the left-edge portion, identified as 24. As the wedge-shaped portion, identified as 26, is folded and lies within the assembled pad during placement and use, it is desirable that the fill not be excessive and uncomfortable. It is desirable that folding and securing be with a minimum of effort and dexterity. The wedge-shaped fold area is shown and discussed in connection with sectional structures later shown and described. As the barrier sheet 10 remains with its initial circular shape, said wedge-shaped portion 26 between edges 22 and 24 is tucked within the pad and edge portion 22. This portion is brought over edge portion 24 to cause a cup shape to be formed. The amount of overlap, indicated as angle 28, is a matter of selection and is made so as to accommodate the depth or shape of the cup provided in the brassiere. Where the cup shape is shallow, the overlap as indicated by angle 28 is less, and where the cup is deeper the overlayed angle 28 is greater.

Figure 3:
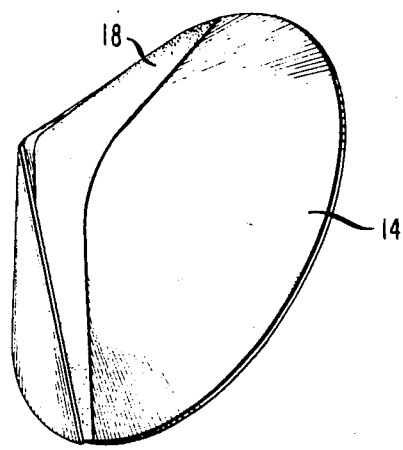
FIG. 3 represents a perspective view of the disposable pad of FIG. 2 and, in particular, depicting the conical formation provided by and with an edge overlap.
Figure 4A:
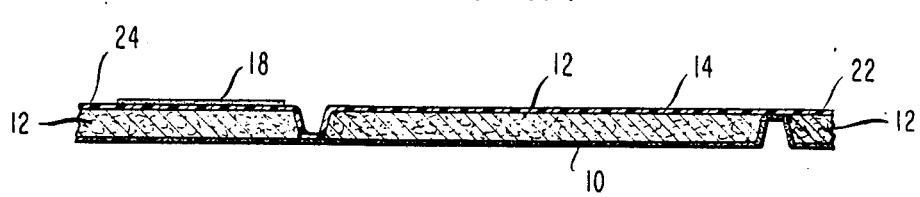
FIGS. 4 A through 4 H represent fragmentary sectional and fold views, partly diagrammatic, and showing the pad in an enlarged scale and with fold arrangements.
Figure 4B:
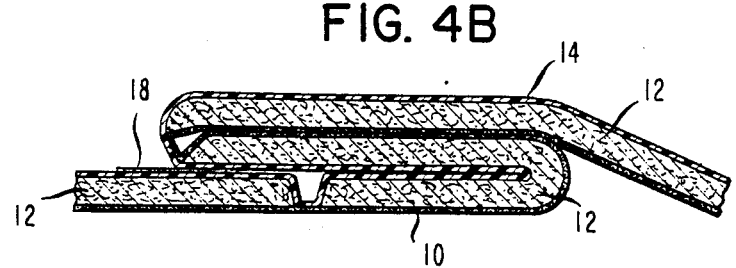
Figure 4C:
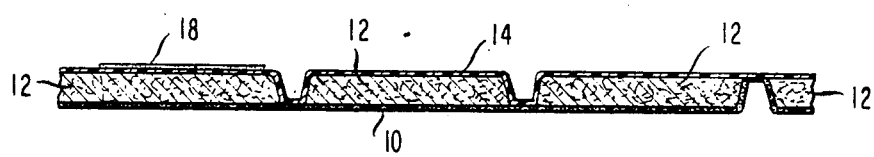
Figure 4D:
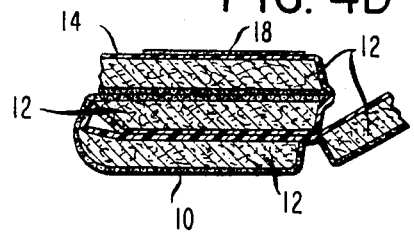
Figure 4E:
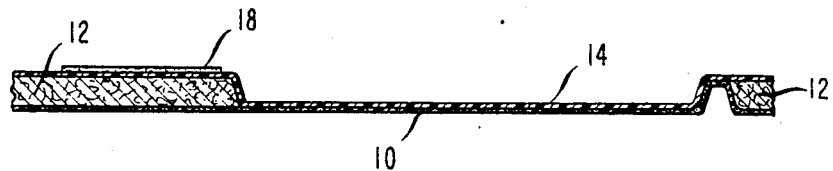
Figure 4F:
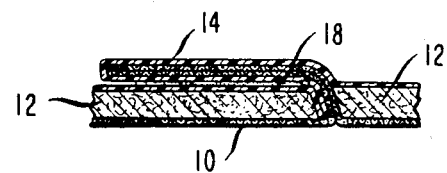

Although a single disposable pad is shown as assembled in FIG. 3, it is, of course, realized that customarily two pads are required and are assembled and used in a brassiere. When the pads are soiled, they are discarded and new pads used. The construction of the pad with a full extent of barrier sheet 10 prevents unwanted leakage of fluids through this barrier sheet. The adhesive 18 is made sufficient for ready securement into the brassiere cup. As and when the pad is removed, it is contemplated that the adhesive 18 be completely or almost completely retained on the barrier sheet 10 so that the brassiere cup be absent adhesive. The fold-over portion 26 is contemplated to be of a minimum bulk. With this in mind, FIGS. 4 A through 4 H are shown, but it is realized that variations are contemplated.

ASSEMBLY AND USE AS IN FIGS. 2 AND 3

As provided for commercial sale and use, the pad of FIG. 1 is planar in configuration and is about four and one-quarter inches in diameter. The edge portion, identified as 20, usually has no fill material provided and is usually from one-quarter to three-eighths of an inch in width, but this is a matter of selection. Manufacturing tolerances and speed are a criteria of this construction.

The adhesive is conventionally applied to the barrier 10 when the strip 16 is brought to and secured to the outer surface of barrier sheet 10. The pads as an article of commerce are packaged and sold in package multiples, such as one dozen. A pad is selected for use as protective liner and the strip 16 is removed and discarded, exposing the adhesive 18. The full length of this adhesive is available, but in forming the cup only the wedge-shaped portions 22 and 24 are utilized. The overlap of edge portion 22 over and on edge portion 24 is made in accordance with individual desire. The conical formation of the pad is more or less in accordance with brassiere to be used. The overlap is made with finger manipulation, and it is of note that the adhesive 18 not covered by the overlap portion is exposed for securing this formed pad within the cup of the brassiere. It is noted that the portion 30, which is not a part of the overlap, is a portion of the fold. The barrier sheet 10 is not cut, which provides unwanted means for leakage. The showing of FIG. 3 is merely diagrammatic as the orientation of the pad in the brassiere cup is a matter of preference. The positioning of the fold as to its exterior and interior orientation in the brassiere cup is a matter of selection and/or preference since the integrity of the barrier member is not altered. The peripheral bonding of the barrier sheet 10 to the cover-sheet member 14 assists in resisting seepage of fluids from the edges of the pad. The impervious barrier sheet insures that the brassiere is not soiled or wetted. The used pad is pulled from the brassiere cup without damage to this brassiere and discarded.

EMBODIMENT OF FIGS. 4 A AND 4 B

In FIG. 4 A is diagrammatically shown a sectional view of the pad in which the fold area 26 includes the barrier sheet 10, the fill 12 and inner cover-sheet member 14. In this showing, a single fold is utilized, with the left edge 24 having adhesive 18 on the exterior surface. The right-edge portion 22 is brought to an overlay position as in FIG. 2. For the purpose of designation, a fold-assist (male and female) is depicted and this designation will be directed as looking from the outside of the pad toward the inside. Male fold-assist lines are identified as 32 and female lines are identified as 34. All such lines are usually localized heat-sealing portions and these formations do not and are not contemplated to alter the moisture-impervious nature of barrier sheet 10.

In FIG. 4 B, the pad of FIG. 1 is partially shown with the pad of FIG. 4 A. From the edge portion 24, the fold area 26 includes a female fold line 34 which is immediately adjacent said edge portion 24, and along this edge and to the left, as viewed, are the adhesive 18 and tear strip 16. This fold line is conventionally made as and with the heat-sealing of the edges of the pad as discussed above. The right-edge portion 22, which provides the overlap, is also provided with a fold assist line 32. This is a male formation and is immediately adjacent the edge 22 and is radially positioned.

The fold area 26 may also be provided with an additional fold-assist to guide the user to fold the pad portion to a mimimum thickness and, where and when provided, is radially disposed and is contemplated to be a male fold line. The overlap of edge 22 over and on edge 24 is contemplated in forming and providing the fold-assist. Conventionally, this additional fold score line is not provided as the pad fill 12 and inner-sheet member 14 are made very thin and pliable.

EMBODIMENT OF FIGS. 4 C AND 4 D

In FIGS. 4 C and 4 D, the fold area 26 is depicted with an additional fold of the pad portion that is retained within and next to the breast. In FIGS. 4 A and 4 B, it is contemplated that the fold area will be disposed to the right of edge 22 as viewed in FIG. 2. If and when the user wishes to fold the pad portion to the left under edge portion 24, an additional fold is required. In FIGS. 4 A and 4 B, there are three thicknesses of pad at the overlap. In FIGS. 4 C and 4 D, there are five thicknesses of the pad at the overlap. This arrangement of layers is shown in FIG. 4 D, although the area of fold excess may be to the left or to the right as desired by the user.

EMBODIMENT OF FIGS. 4 E AND 4 F

In this emobdiment, it is contemplated that the pad be made with an absence of fill in the fold area. For the purpose of identification, the fragmentary plan view of such a pad has the right edge identified as 50 and the left-edge portion as 52, with the assembled pad identified as 54. The folding will be like that shown in FIGS. 4 A and B, absent a fill 12 but with the barrier sheet 10 and cover sheet 14 present as in FIG. 1. Absent a fill 12, the fold area is more easily manipulated as a portion of the bulk has been eliminated. Since manufacturing problems may be present with the removal or absence of a portion of fill, this showing is merely indicative of an alternate arrangement. It is to be noted that fold-assists are provided in heat-sealed lines which are shown with both male and female fold-assists. Using the fold arrangement of FIG. 4 A, where three thicknesses are present at the overlap of edge 50 over and on edge 52, the fold portion, identified as 58, is arrayed to the right and under the barrier sheet 10. The three thicknesses of material at the overlap now include the fold portion absent fill 12 so the thickness is less by the amount of fill.

In FIG. 4 F, the embodiment of FIG. 4 E is repeated but, instead of the fold-portion area 58 to the right, the folded portion is arrayed to the left. When this occurs, there are five thicknesses at the overlap area. This fold portion 58 is absent fill 12 so that when arrayed with five thicknesses, the absence of fill 12 reduces the amount of fold material within the brassiere cup.

EMBODIMENT OF FIGS. 4 G AND 4 H

Referring next to the embodiments of FIGS. 4 G and 4 H, the removable pad is depicted as made with the barrier sheet 10 as an inviolate member and with fill 12 and cover-sheet member 14 absent at the fold extent. For this purpose of identification, the right-edge portion is identified as 60 and the left-edge portion as 62. The pad is identified as 64, with the fold area absent fill 12 and cover-sheet member portion 14. This pad is similar to that shown in FIGS. 4 A or 4 B, with this fold area having only the barrier sheet 10, and identified as 66.

In FIG. 4 G, the right-edge portion 60, when brought to and secured to the adhesive portion 18, is in overlay condition and position and the cover portion 68 therebetween is folded so that an immediately adjacent portion is in retaining contact with said adhesive 18. In FIG. 4 G, the fold portion is shown to the right and under portion 60. In FIG. 4 H, the fold area 66 is folded and extends to the left and under edge portion 62. With and when the fold area includes only the barrier sheet 10, even five thicknesses are only a small amount.

EMBODIMENT OF FIGS. 5 A, 5 B AND 5 C

Referring next to the sectional and diagrammatic views in FIGS. 5 A, 5 B and 5 C, the showing depicts heat-sealing dies as utilized for making and forming fold-assists. In FIG. 5 A, there are shown both male and female score lines for the securing of barrier film 10 to cover sheet 14. In FIG. 5 A, the fill 12 is present and, as depicted, a male seal 32 is formed with a protruding die portion 70 adapted to form a male seal 32. The female seal 34 is formed with a protruding die portion 72. It is, of course, realized that the protrusions 70 and 72 are only for the score-line portions, and the extent, shape and position are selected to accommodate the pad to be produced. The composition and thickness of the barrier sheet 10, the fill 12 and cover member 14 is a consideration. A heated back or support die is not shown as heat-sealing and details thereof are conventional and are conformed by the maker of the dies.

In FIG. 5 B, the pad is made absent a fill 12 and, at the fold area, die 70 forms a seal line, now identified as 132, disposed adjacent the right edge of the pad. A seal line 134 is also provided at the left edge of the fold area. This fold portion between seal lines is identified as 128 and includes barrier sheet 10 and cover-member portion 14. The fold area 128 may or may not have the barrier 10 secured to cover member 14.

In FIG. 5 C, the pad is made absent fill 12 and cover member 14 in and at the fold area. Dies 70 and 72 are utilized as described above. The fold area, identified as 228, is only with the barrier sheet 10. As the fill area and cover sheet are required at these right and left edges, they must still utilize the dies 70 and 72 to form male and female grooves, identified as 232 and 234. The cover-sheet member 14 is shown with the fill 12 at these edges. The cover sheet 14 extends toward the fold area 228 sufficiently to provide material for making the heat-seal.

EMBODIMENT OF FIG. 6

FIG. 6 is a fragmentary sectional side view indicating a fluff or soft edge that is deliberately produced so that an extending portion of the soft fill extends beyond the edge of barrier 10 of the pad and provides soft outer edges to the pad. As depicted fragmentarily, barrier film 10 is arrayed with fill 12 and cover 14. The pad is sealed peripherally at 20 and, as shown, a small portion of fill, identified as 112, is caused to extend beyond this peripheral seal to provide a soft edge as may be desired where and when the breast is tender and easily irritated.

It is to be noted that the seal 116 is made immediately adjacent edge 24 and immediately to the left of this seal is placed the tear strip 16 carrying adhesive 18. This seal 116 establishes the orientation of the strip 18 no matter the construction of the pad whether as in FIGS. 4 A through 4 H or the constructions shown in FIGS. 5 A, B, and C, and FIG. 6. The adhesive 16 is applied conventionally to the barrier sheet 10 with the securing of strip 18 in position, but this width and securing is merely a matter of selection as technology is rapidly changing and high-speed automatic production means are contemplated. As this is a disposable pad, economy of structure and manufacture is essential. The adhesive may be of a greater area than shown, but a release sheet for such adhesive is required with each pad to prevent unwanted sticking of the pads to themselves.

The forming of the pad with a soft-edge fill 112 (FIG. 6) which protrudes a small amount is a matter of design. Soft-edge formation may be desired for some disposable pads provided for certain users and not required for other users. Soft edges are contemplated when and where the user's skin is particularly tender or easily irritated. The folding of the pad edges and the resulting overlap may cause localized areas to be susceptible to irritation. For this reason, alternate constructions are illustrated. The fold area may have fold-assists in the form of seal lines, but this is merely a matter of preference.

Adhesive may be used to retain the fill 12 on the barrier sheet 10 during manufacturing. This same adhesive may be employed to assist in the retention of the cover material 14 to the barrier sheet 10 prior to the sealing of the edges and establishing of fold score-assists. The fold-assists shown and described as male and female may be reversed as to location, with these scores conventionally produced with heat-sealing dies. The use of sonic welding is also contemplated and pressure-sealing is also contemplated. Whether the fold is to be made to the right or left is merely a matter of selection as is the absence of fill 12 as in FIG. 5 B.

The score lines establish retention of the fill 12 in the resulting pad and the included angle, but making the fold is a matter of design. It is to be noted that the adhesive 18 in the shown embodiments is not present in the fold area, but is present immediately adjacent the fold score-assist lines. In providing a soft edge 112 as in FIG. 6, the added fill may be included in the fill layer 12 or may be a ring portion additionally supplied. The fold area may be as depicted in FIGS. 5 A, 5 B or 5 C, with this construction selected by the manufacturer of the pad.

EMBODIMENT OF FIGS. 7 AND 8

Referring next to the embodiment shown in FIGS. 7 and 8, it is to be noted that the pad as shown in FIGS. 1 through 3 may have added pressure-induced portions that provide assists in forming the pad into a cup shape. The showing in FIG. 7 has pressurized lines, identified as 80, which are pressure-induced score lines absent heat-sealing of the cover 10 to the impervious backing sheet 14. The fill 12 may be slightly reduced in thickness, but the absorbing capability and transferance capacity (wicking) is not diminished. The outer rim portion 82 is devoid of fill 12 and is heat-sealed or otherwise secured together to provide a seal and barrier to an outflow of fluids received and retained in and by the pad. As in FIGS. 1 through 3, the pad is provided with adhesive 18 and tear strip 15. This pad, in addition to pressure-induced lines 80, may also be provided with male and female radially-disposed heat-seals 32 and 34, as seen in FIG. 4 C. The pressure-formed portion 80 is also depicted in the sectional view of FIG. 8.

EMBODIMENT OF FIG. 9

The showing in FIG. 9 is to disclose that the cover material 10 may have a multiplicity of punctures 90 formed therein and therethrough. These punctures are formed by pins to provide a plurality of one-way passageways at the time of producing this cover. Alternately, these punctures 90 are provided or applied as when the pad is assembled and made. The adding of punctures 90 to the cover 10 assists in the passing therethrough of fluids. The absorbency is provided by fill 12. Cover 10 may also have absorbent capability, but the added punctures or apertures 90 increase the passing of fluids through the cover 10 into the fill 12. The barrier sheet 14 is and has been described above.

The above disclosure also provides a basis of and for a method of manufacture and use of the disposable breast pad, this pad having a generally circular configuration and having a locally pie-shaped portion provided with assist score lines, which portion is adapted to be folded to provide a cup-shaped pad which is removably mounted by self-adhesion to an inner concave portion of a brassiere, said method steps including:

providing a thin, pliable, impervious barrier layer having thermoplastic properties;

carrying a layer of high-absorbency fill material by and in contiguous relationship to the barrier layer and configuring this fill material so as to be a defined distance interior of the edges of barrier layer;

supplying and placing a relatively thin top cover layer of porous material and having thermoplastic properties and securing substantially continuously said top layer at its peripheral edges to the edges of the barrier layer;

applying a non-toxic contact-adhesive to the outer surface of said barrier layer to at least provide a defined strip;

providing a pull-away release-sheet portion sized and configured to cover that contact-adhesive disposed on the barrier layer, this contact-adhesive disposed to remain on the barrier layer during use of the pad, this contact-adhesive providing sufficient adhesion to retain the shaped pad within a brassiere cup and with said adhesive disposed to remain on the barrier layer when and as the used pad is removed from the brassiere cup and discarded, and forming male and female fold score lines in a radial array, with each score line defining a radially-disposed edge portion extending from the periphery of the pad toward the center of the pad, said score lines defining and assisting in a folding of a localized pie-shaped portion, said localized folding including the removal of the release sheet from the adhesive applied to the outer surface of the barrier sheet, the folding and manipulating including bringing one radial edge over the other edge to provide an overlap at the outer peripheral extent and utilizing that portion of the adhesive at the peripheral portion of the pad for retaining the folding overlap.

Terms such as "left," "right," "up," "down," "bottom," "top," "front," "back," "in," "out," and the like are applicable to the embodiments shown and described in conjunction with the drawings. These terms are merely for the purposes of description and do not necessarily apply to the position in which the disposable, sanitary breast pad may be constructed or used.

While a particular embodiment of the disposable pad for mounting in a brassiere and alternate embodiments have been shown and described, it is to be understood that the invention is not limited thereto and protection is sought to the broadest extent the prior art allows.

What is claimed is:

1. A flat, disposable breast pad of a generally circular configuration and having a locally pie-shaped portion provided with assist score lines, which portion is adapted to be folded to provide a cup-shaped pad which is removably mounted by self-adhesion to an inner concave portion of a brassiere, said pad including:

(a) a thin, pliable, impervious barrier layer having thermoplastic properties;

(b) a layer of high-absorbency fill material carried by and in contiguous relationship to the barrier layer, this fill material configured so as to be a defined distance interior of the edges of barrier layer;

(c) a relatively thin top cover layer of porous material and having thermoplastic properties and being substantially continuously secured at its peripheral edges to the edges of the barrier layer;

(d) a non-toxic contact-adhesive applied to the outer surface of said barrier layer to at least provide a defined strip;

(e) a pull-away release-sheet portion sized and configured to cover that contact-adhesive disposed on the barrier layer, this contact-adhesive disposed to remain on the barrier layer during use of the pad, this contact-adhesive providing sufficient adhesion to retain the shaped pad within a brassiere cup and with said adhesive disposed to remain on the barrier layer when and as the used pad is removed from the brassiere cup and discarded, and (f) male and female fold score lines formed in a radial array, each score line defining a radially-disposed edge portion extending from the periphery of the pad toward the center of the pad, the score lines to define and assist in a folding of a localized pie-shaped portion, said localized folding including the removal of the release sheet from the adhesive applied to the outer surface of the barrier sheet, the folding and manipulating including bringing one radial edge over the other edge to provide an overlap at the outer peripheral extent and utilizing that portion of the adhesive at the peripheral portion of the pad for retaining the folding overlap.

2. A flat, disposable breast pad as in claim 1 in which the fold area includes the thin, pliable barrier layer, a contiguous fill layer except for the defined edge portion, and said thin top cover layer, and with the adhesive applied as a strip immediately adjacent that fold score line for the edge portion providing the inner one-half of the overlap.

3. A flat, disposable breast pad as in cliam 2 in which the strip of applied adhesive is at least one-quarter inch in width, said strip extending from one edge to an opposite edge on the pad, this adhesive disposed to the barrier layer so as to be in that area other than in the fold area.

4. A flat, disposable breast pad as in claim 1 in which the fold area includes the thin, pliable barrier layer, an absence of fill material, and said thin top cover layer of porous material.

5. A flat, disposable breast pad as in claim 1 in which the fold area includes substantially only the thin barrier layer.

6. A flat, disposable breast pad as in claim 1 which includes forming additional pressure-induced fold assist lines, these assist lines radially-disposed.

7. A flat, disposable breast pad as in claim 1 which includes providing in the relatively thin top cover layer additional small apertures or prick-type openings which are adapted to provide increased flow means.

8. A flat, disposable breast pad of a generally circular configuration and having a locally pie-shaped portion provided with assist score lines, which portion is adapted to be folded to provide a cup-shaped pad which is removably mounted by self-adhesion to an inner concave portion of a brassiere, said pad including:

(a) a thin, pliable, impervious barrier layer having thermoplastic properties;

(b) a layer of high-absorbency fill material carried by and in contiguous relationship to the barrier layer, this fill material of a thickness so as to be sealed at the edges of barrier layer;

(c) a relatively thin top cover layer of porous material and having thermoplastic properties and being substantially continuously secured at its peripheral edges to the edges of the barrier layer;

(d) an outwardly-extending fill portion disposed to be retained with the sealing of the barrier layer to the top layer, this extending fill portion disposed to provide a soft-edge exterior of the sealed edges of the pad;

(e) a non-toxic contact-adhesive applied to the outer surface of said barrier layer to at least provide a defined strip;

(f) a pull-away release-sheet portion sized and configured to cover that contact-adhesive disposed on the barrier layer, this contact-adhesive disposed to remain on the barrier layer during use of the pad, this contact-adhesive providing sufficient adhesion to retain the shaped pad within a brassiere cup and with said adhesive disposed to remain on the barrier layer when and as the used pad is removed from the brassiere cup and discarded, and (g) male and female fold score lines formed in a radial array, each score line defining a radially-disposed edge portion extending from the periphery of the pad toward the center of the pad, the score lines to define and assist in a folding of a localized pie-shaped portion, said localized folding including the removal of the release sheet from the adhesive applied to the outer surface of the barrier sheet, the folding and manipulating including bringing one radial edge over the other edge to provide an overlap at the outer peripheral extent and utilizing that portion of the adhesive at the peripheral portion of the pad for retaining the folding overlap.

9. A flat, disposable breast pad as in claim 8 in which the fold area includes the thin, pliable barrier layer, a contiguous fill layer except for the defined edge portion, and said thin top cover layer, and with the adhesive applied as a strip immediately adjacent that fold score line for the edge portion providing the inner one-half of the overlap.

10. A flat, disposable breast pad as in claim 9 in which the strip of applied adhesive is at least one-quarter inch in width, said strip extending from one edge to an opposite edge on the pad, this adhesive disposed to the barrier layer so as to be in that area other than in the fold area.

11. A flat, disposable breast pad as in claim 8 in which the fold area includes the thin, pliable barrier layer, an absence of fill material, and said thin top cover layer of porous material.

12. A flat, disposable breast pad as in claim 8 in which the fold area includes substantially only the thin barrier layer.

13. A flat, disposable breast pad as in claim 8 which includes forming additional pressure-induced fold assist lines, these assist lines radially-disposed.

14. A flat, disposable breast pad as in claim 8 which includes providing in the relatively thin top cover layer additional small apertures or prick-type openings which are adapted to provide increased flow means.

15. A method of manufacturing a flat, disposable breast pad of a generally circular configuration and having a locally pie-shaped portion provided with assist score lines, which portion is adapted to be folded to provide a cup-shape, and removably mounting said pad by self-adhesion to an inner concave portion of a brassiere, said method including the steps of:

(a) providing a thin, pliable, impervious barrier layer having thermoplastic properties;

(b) carrying a layer of high-absorbency fill material by and in contiguous relationship to the barrier layer and configuring this fill material so as to be a defined distance interior of the edges of barrier layer;

(c) supplying and placing in an arrayed manner a relatively thin top cover layer of porous material having thermoplastic properties and securing said cover member substantially continuously at its peripheral edges to the edges of the barrier layer;

(d) applying a non-toxic contact-adhesive to the outer surface of said barrier layer to at least provide a defined strip;

(e) providing a pull-away release-sheet portion sized and configured to cover that contact-adhesive disposed on the barrier layer, this contact-adhesive disposed to remain on the barrier layer during use of the pad, this contact-adhesive providing sufficient adhesion to retain the shaped pad within a brassiere cup and with said adhesive disposed to remain on the barrier layer when and as the used pad is removed from the brassiere cup and discarded, and (f) forming male and female fold score lines in a radial array, with each score line defining a radially-disposed edge portion extending from the periphery of the pad toward the center of the pad, said score lines defining and assisting in a folding of a localized pie-shaped portion, said localized folding including the removal of the release sheet from the adhesive applied to the outer surface of the barrier sheet, the folding and manipulating including bringing one radial edge over the other edge to provide an overlap at the outer peripheral extent and utilizing that portion of the adhesive at the peripheral portion of the pad for retaining the folding overlap.

16. A method of manufacturing a flat, disposable breast pad as in claim 15 which includes forming the fold area with the thin, pliable barrier layer; a contiguous fill layer except for the defined edge portion, and a thin top cover attached to the edge of barrier layer, and applying said adhesive as a strip immediately adjacent that fold score line formed for that edge portion providing the inner one-half of the overlap.

17. A method of manufacturing a flat, disposable breast pad as in claim 16 which includes forming the adhesive strip with at least one-quarter inch width and extending said adhesive strip from one peripheral edge to an opposite side of the pad, and disposing this adhesive on the barrier layer so as to be in an area other than the fold area.

18. A method of manufacturing a flat, disposable breast pad as in claim 15 which includes forming the fold area with the thin, pliable barrier layer; an absence of fill material, and a cover layer of porous material.

19. A method of manufacturing a flat, disposable breast pad as in claim 15 which includes forming the fold area with substantially only the thin barrier layer.

20. A method of manufacturing a flat, disposable breast pad as in claim 15 which includes forming the pad with additional radially-disposed pressure-induced fold assist lines.

21. A method of manufacturing a flat, diposable breast pad as in claim 15 which includes forming in the thin top cover layer additional small apertures or prick-type openings which provide increased fluid flow paths.

* * * * *